United States Patent
Dollevoet et al.

(10) Patent No.: US 10,660,802 B2
(45) Date of Patent: May 26, 2020

(54) ABSORBENT ARTICLE SIDE PANEL METHOD OF FASTENING

(71) Applicant: Kimberly-Clark Worldwide, Inc., Neenah, WI (US)

(72) Inventors: Tim G. Dollevoet, Kimberly, WI (US); Timothy L. Smith, Fod du Lac, WI (US); Andrew Edward Neubauer, Neenah, WI (US); Bradley A. Colvin, Appleton, WI (US); Cole W. Poole, Appleton, WI (US); John Dibb, Madison, WI (US)

(73) Assignee: KIMBERLY-CLARK WORLDWIDE, INC., Neenah, WI (US)

( * ) Notice: Subject to any disclaimer, the term of this patent is extended or adjusted under 35 U.S.C. 154(b) by 442 days.

(21) Appl. No.: 15/572,803

(22) PCT Filed: Dec. 28, 2016

(86) PCT No.: PCT/US2016/068794
§ 371 (c)(1),
(2) Date: Nov. 9, 2017

(87) PCT Pub. No.: WO2017/117172
PCT Pub. Date: Jul. 6, 2017

(65) Prior Publication Data
US 2018/0104111 A1 Apr. 19, 2018

Related U.S. Application Data

(60) Provisional application No. 62/272,846, filed on Dec. 30, 2015.

(51) Int. Cl.
*A61F 13/15* (2006.01)
*A61F 13/496* (2006.01)
*A61F 13/56* (2006.01)

(52) U.S. Cl.
CPC .. *A61F 13/15739* (2013.01); *A61F 13/15747* (2013.01); *A61F 13/15804* (2013.01); *A61F 13/4963* (2013.01); *A61F 13/565* (2013.01)

(58) Field of Classification Search
None
See application file for complete search history.

(56) References Cited

U.S. PATENT DOCUMENTS

| | | |
|---|---|---|
| 507,485 A | 10/1893 | Carr et al. |
| 3,685,818 A | 8/1972 | Burger et al. |
| 3,773,214 A | 11/1973 | Lemon |
| 3,875,621 A | 4/1975 | Karami |
| 3,951,149 A | 4/1976 | Ness et al. |
| 3,994,486 A | 11/1976 | Nystrand |

(Continued)

FOREIGN PATENT DOCUMENTS

| | | |
|---|---|---|
| EP | 0 217 032 A2 | 4/1987 |
| JP | 11-043801 A | 2/1999 |

(Continued)

*Primary Examiner* — Barbara J Musser
(74) *Attorney, Agent, or Firm* — Kimberly-Clark Worldwide, Inc.

(57) ABSTRACT

A method of manufacturing an absorbent article which is prefastened by the manufacturer and refastenable by the wearer of the absorbent article. The method can include fastening the side panels of an absorbent article in which the side panels of the absorbent article are of different widths.

13 Claims, 7 Drawing Sheets

(56) References Cited

U.S. PATENT DOCUMENTS

| | | |
|---|---|---|
| 4,100,324 A | 7/1978 | Anderson et al. |
| 4,610,680 A | 9/1986 | Lafleur |
| 4,619,649 A | 10/1986 | Roberts |
| 4,663,220 A | 5/1987 | Wisneski et al. |
| 4,747,846 A | 5/1988 | Boland et al. |
| 4,795,510 A | 1/1989 | Wittrock et al. |
| 4,850,988 A | 7/1989 | Aledo et al. |
| 4,909,804 A | 3/1990 | Douglas, Sr. |
| 4,940,464 A | 7/1990 | Van Gompel et al. |
| 5,046,272 A | 9/1991 | Vogt et al. |
| 5,053,028 A | 10/1991 | Zoia et al. |
| 5,094,658 A | 3/1992 | Smithe et al. |
| 5,104,116 A | 4/1992 | Pohjola |
| 5,163,932 A | 11/1992 | Nomura et al. |
| 5,224,405 A | 7/1993 | Pohjola |
| 5,226,992 A | 7/1993 | Morman |
| 5,284,703 A | 2/1994 | Everhart et al. |
| 5,350,624 A | 9/1994 | Georger et al. |
| 5,385,775 A | 1/1995 | Wright |
| 5,486,166 A | 1/1996 | Bishop et al. |
| 5,490,846 A | 2/1996 | Ellis et al. |
| 5,531,732 A | 7/1996 | Wood |
| 5,624,420 A | 4/1997 | Bridges et al. |
| 5,705,013 A | 1/1998 | Nease et al. |
| 5,820,973 A | 10/1998 | Dodge, II et al. |
| 5,827,260 A | 10/1998 | Suzuki et al. |
| 6,004,306 A | 12/1999 | Robles et al. |
| 6,057,024 A | 5/2000 | Mleziva et al. |
| 6,213,991 B1 | 4/2001 | Kling et al. |
| 6,302,871 B1 | 10/2001 | Nakao et al. |
| 6,447,628 B1 | 9/2002 | Couillard et al. |
| 6,481,362 B2 | 11/2002 | Hietpas et al. |
| 6,525,238 B2 | 2/2003 | Corrales |
| 6,596,113 B2 | 7/2003 | Csida et al. |
| 6,746,433 B1 | 6/2004 | Shimoe et al. |
| 6,854,624 B2 | 2/2005 | Vogt et al. |
| 6,875,710 B2 | 4/2005 | Eaton et al. |
| 6,916,750 B2 | 7/2005 | Thomas et al. |
| 6,968,992 B2 | 11/2005 | Schuster |
| 6,969,441 B2 | 11/2005 | Welch et al. |
| 7,156,834 B2 | 1/2007 | Kawata et al. |
| 7,175,584 B2 | 2/2007 | Maxton et al. |
| 7,217,260 B2 | 5/2007 | Molander et al. |
| 7,255,688 B2 | 8/2007 | Sasaki et al. |
| 7,322,925 B2 | 1/2008 | Couillard et al. |
| 7,335,150 B2 | 2/2008 | Coenen et al. |
| 7,387,148 B2 | 6/2008 | Vogt et al. |
| 7,452,320 B2 | 11/2008 | Csida et al. |
| 7,534,481 B2 | 5/2009 | Seth et al. |
| 7,744,577 B2 | 6/2010 | Otsubo et al. |
| 7,803,244 B2 | 9/2010 | Siqueira et al. |
| 7,806,880 B2 | 10/2010 | Roe et al. |
| 7,887,522 B2 | 2/2011 | Roe et al. |
| 7,985,210 B2 | 7/2011 | Ashton et al. |
| 8,034,040 B2 | 10/2011 | Sasaki et al. |
| 8,066,687 B2 | 11/2011 | Ashton et al. |
| 8,235,962 B2 | 8/2012 | Popp et al. |
| 8,262,636 B2 | 9/2012 | Sperl |
| 8,337,479 B2 | 12/2012 | Nilsson et al. |
| 8,361,913 B2 | 1/2013 | Siqueira et al. |
| 8,556,790 B2 | 10/2013 | Fujita |
| 8,821,360 B2 | 9/2014 | Umebayashi |
| 8,936,586 B2 | 1/2015 | Roe |
| 8,939,876 B2 | 1/2015 | Schneider et al. |
| 2002/0111596 A1 | 8/2002 | Fletcher et al. |
| 2002/0138059 A1 | 9/2002 | Van Gompel et al. |
| 2003/0087059 A1 | 5/2003 | Jackson et al. |
| 2004/0186451 A1 | 9/2004 | Bishop et al. |
| 2005/0130821 A1 | 6/2005 | Reising et al. |
| 2005/0175269 A1 | 8/2005 | Ashton et al. |
| 2006/0025737 A1 | 2/2006 | Song et al. |
| 2006/0155255 A1 | 7/2006 | McKiernan et al. |
| 2006/0167434 A1 | 7/2006 | Ashton et al. |
| 2007/0029035 A1 | 2/2007 | Desai et al. |
| 2007/0083177 A1 | 4/2007 | Takino et al. |
| 2007/0233033 A1 | 10/2007 | Ichikawa et al. |
| 2008/0045918 A1 | 2/2008 | Driskell |
| 2008/0108963 A1 | 5/2008 | Ashton et al. |
| 2008/0114322 A1 | 5/2008 | Schmoker et al. |
| 2009/0149827 A1 | 6/2009 | Mlinar et al. |
| 2010/0004616 A1 | 1/2010 | Nakamura et al. |
| 2011/0313380 A1 | 12/2011 | Ashton et al. |
| 2012/0101463 A1 | 4/2012 | Sperl |
| 2012/0101468 A1 | 4/2012 | Sperl |
| 2012/0157953 A1 | 6/2012 | Ashton et al. |
| 2012/0208688 A1 | 8/2012 | Sakaguchi et al. |
| 2012/0225764 A1 | 9/2012 | Ogasawara |
| 2013/0231629 A1 | 9/2013 | Paveletzke et al. |
| 2014/0228192 A1 | 8/2014 | Schuster |
| 2015/0144251 A1 | 5/2015 | Schoultz et al. |

FOREIGN PATENT DOCUMENTS

| | | |
|---|---|---|
| JP | 11-104180 A | 4/1999 |
| JP | 2008-212485 A | 9/2008 |
| JP | 2012-075458 A | 4/2012 |
| WO | WO 1989/007897 A1 | 9/1989 |
| WO | WO 1998/013002 A1 | 4/1998 |
| WO | 0187562 A2 | 11/2001 |
| WO | WO 2001/088245 A2 | 11/2001 |

ABSORBENT ARTICLE SIDE PANEL METHOD OF FASTENING

RELATED APPLICATIONS

The present application claims priority to U.S. Provisional Application No. 62/272,846, which was filed on Dec. 30, 2015, the contents of which are hereby incorporated by reference in a manner consistent with the present application.

BACKGROUND OF THE DISCLOSURE

Garments such as disposable absorbent articles have numerous applications including diapers, training pants, feminine care products, and adult incontinence products. The typical disposable absorbent article is formed as a composite structure including an absorbent assembly disposed between a liquid permeable bodyside liner and a liquid impermeable outer cover. These components can be combined with other materials and features such as elastic materials and containment structures to form a product that is specifically suited to its intended purpose.

One form of a disposable absorbent article is a two-dimensional product that has open sides. Two-dimensional products, such as conventional diapers and some adult incontinence products, are generally flat and provided in an unfastened configuration. These absorbent articles have typically included fasteners such as adhesive tape fasteners or hook and loop type fasteners that releasably connect the front and back waist portions to secure the absorbent article about the wearer. Two-dimensional absorbent articles can be easily applied or removed while the wearer is lying down.

Another form of a disposable absorbent article is a three-dimensional absorbent article with closed sides so that the absorbent article has a unitary waist opening and two leg openings. The wearer raises and lowers the absorbent article to apply the absorbent article. Three-dimensional absorbent articles are particularly appealing because the absorbent article has a garment-like look. Children, for instance, identify diaper products with babies and most children do not want to wear baby diapers, and instead prefer to wear absorbent articles such as training pants that look like adult underwear. Thus, the switch from a traditional diaper to a more garment-like or underwear-like training pant can be an important step in the toilet training process. Similarly, adults seeking the protection of incontinence products prefer the normalcy of a pant product rather than an incontinence product that must be applied in another fashion. Three-dimensional absorbent articles have been designed such that they can be torn to remove the absorbent article from the wearer after it has been soiled.

Recently, prefastened and refastenable disposable absorbent articles have been proposed to provide the advantages of both two-dimensional and three-dimensional absorbent articles. Prefastened and refastenable absorbent articles can be applied and/or removed either like a conventional diaper or like a conventional training pant. For use as training pants, for example, there may be times when it would be useful to apply the product like a diaper. For instance, it might be more convenient to apply the absorbent article like a diaper when there is a desire not to remove the child's shoes. Because it is difficult to known when a particular mode of applying the absorbent article will be needed, it is beneficial to have an absorbent article that is adaptable to being used either as a diaper or as a pant. This is preferable to keeping both types of absorbent articles available. An absorbent article that can be applied like either a diaper or a pant permits the interior of the absorbent article to be easily checked without having to pull the product downward.

Disposable absorbent articles present many manufacturing challenges. In part, this is due to the high speed that is necessary to economically produce relatively low cost disposable absorbent articles. Further, prefastened and refastenable absorbent articles present new challenges for high speed manufacturing. Such products must incorporate refastenable fasteners that are properly aligned and engaged. Improperly aligned and or engaged fasteners can lead to many product deficiencies, including machine waste and/or delay, improper fit, fastener delamination during use, fastener disengagement during use, skin irritation, or the like.

Generally, the prefastened and refastenable seams of such absorbent articles have been placed in the absorbent article such that they will be relatively centered at the side of the wearer of the absorbent article. In many instances, it may be desirable for the wearer of the absorbent article to be able to exert control over the donning and removal of the absorbent article and, in such instances, the prefastened and refastenable seams of the absorbent article need to be located in positions where it will be easier for the wearer to open the seams. Such locations tend to be closer to the front of the wearer rather than the approximate side of the wearer. To place the prefastened and refastenable seams at such locations requires that a pair of side panels which ultimately form the sides of the absorbent article be larger than the other pair of side panels. For example, the back side panels can have a width dimension, measured in the lateral direction of the absorbent article, which is larger than the width dimension of the front side panels. In such an example, the prefastened and refastenable seams will be positioned closer to the front waist region of the absorbent article.

Conventional manufacturing techniques for making conventional absorbent articles, including those absorbent articles with centered prefastened and refastenable side seams, are, in many respects, inadequate to handle an absorbent article with side panels of differing width dimensions.

There is need for a manufacturing process which can fasten and engage the fastening mechanisms positioned on side panels of differing width dimensions.

SUMMARY OF THE DISCLOSURE

A method of forming a side seam of an absorbent article, the method comprising the steps of providing an absorbent article comprising a machine direction, a cross-direction, and a z-direction; a front waist region, a back waist region, and a crotch region extending between and connecting the front waist region and the back waist region; a first side panel comprising a first fastening component and located in the front waist region having a first width dimension in the cross-direction; and a second side panel comprising a second fastening component and located in the back waist region having a second width dimension in the cross-direction, wherein the second width dimension is larger than the first width dimension; bringing the first side panel and the second side panel into proximity with each other; folding the second side panel over the first side panel; engaging the first fastening component and the second fastening component in the z-direction; and manipulating the first side panel and the second side panel in the cross-direction to further engage the first fastening component and the second fastening component in the cross-direction.

In various embodiments, the first side panel and the second side panel are brought into proximity by folding the absorbent article. In various embodiments, the second side panel is a back side panel of the absorbent article. In various embodiments, the first side panel is a front side panel of the absorbent article. In various embodiments, the engagement is one of an adhesive engagement or a hook and loop engagement. In various embodiments, the folding of the second side panel occurs via compressed air.

In various embodiments, the absorbent article is transported in a machine direction of the method and between a pair of fastening conveyors. In various embodiments, one of the fastening conveyors has a fold plate around which the second side panel folds. In various embodiments, the first side panel and the second side panel pass between a belt of the fastening conveyor and the fold plate of the fastening conveyor. In various embodiments, the second side panel extends in the cross-direction beyond the fold plate. In various embodiments, the pair of fastening conveyors further have a pair of engagement rollers. In various embodiments, the fastening conveyor further has an engagement rod. In various embodiments, the engagement rod has an arch in the cross-direction.

Repeat use of reference characters in the present specification and drawings is intended to represent the same or analogous features or elements of the disclosure.

DETAILED DESCRIPTION OF THE DISCLOSURE

The disclosure herein is generally directed towards a method of manufacturing an absorbent article which is prefastened by the manufacturer and refastenable by the wearer of the absorbent article. The disclosure herein is generally directed towards fastening the side panels of an absorbent article in which the side panels of the absorbent article are of different widths.

Definitions

The term "bonded" refers herein to the joining, adhering, connecting, attaching, or the like, of two elements. Two elements will be considered bonded together when they are joined, adhered, connected, attached, or the like, directly to one another or indirectly to one another, such as when each is directly bonded to intermediate elements. The bonding of one element to another can occur via continuous or intermittent bonds. The bonding of one element to another can occur via any suitable means such as, but not limited to, adhesives, ultrasonic bonds, thermal bonds, pressure bonds, or other conventional techniques. An adhesive can be applied continuously or intermittently as beads, a spray, parallel swirls, or the like. Suitable adhesives can be obtained from Bostik Findlay Adhesives, Inc. of Wauwatosa, Wis., U.S.A.

The term "cross direction" refers herein to the width of a fabric in a direction generally perpendicular to the direction in which it is produced, as opposed to "machine direction" that refers to the length of a fabric in the direction in which it is produced.

Figure 1:
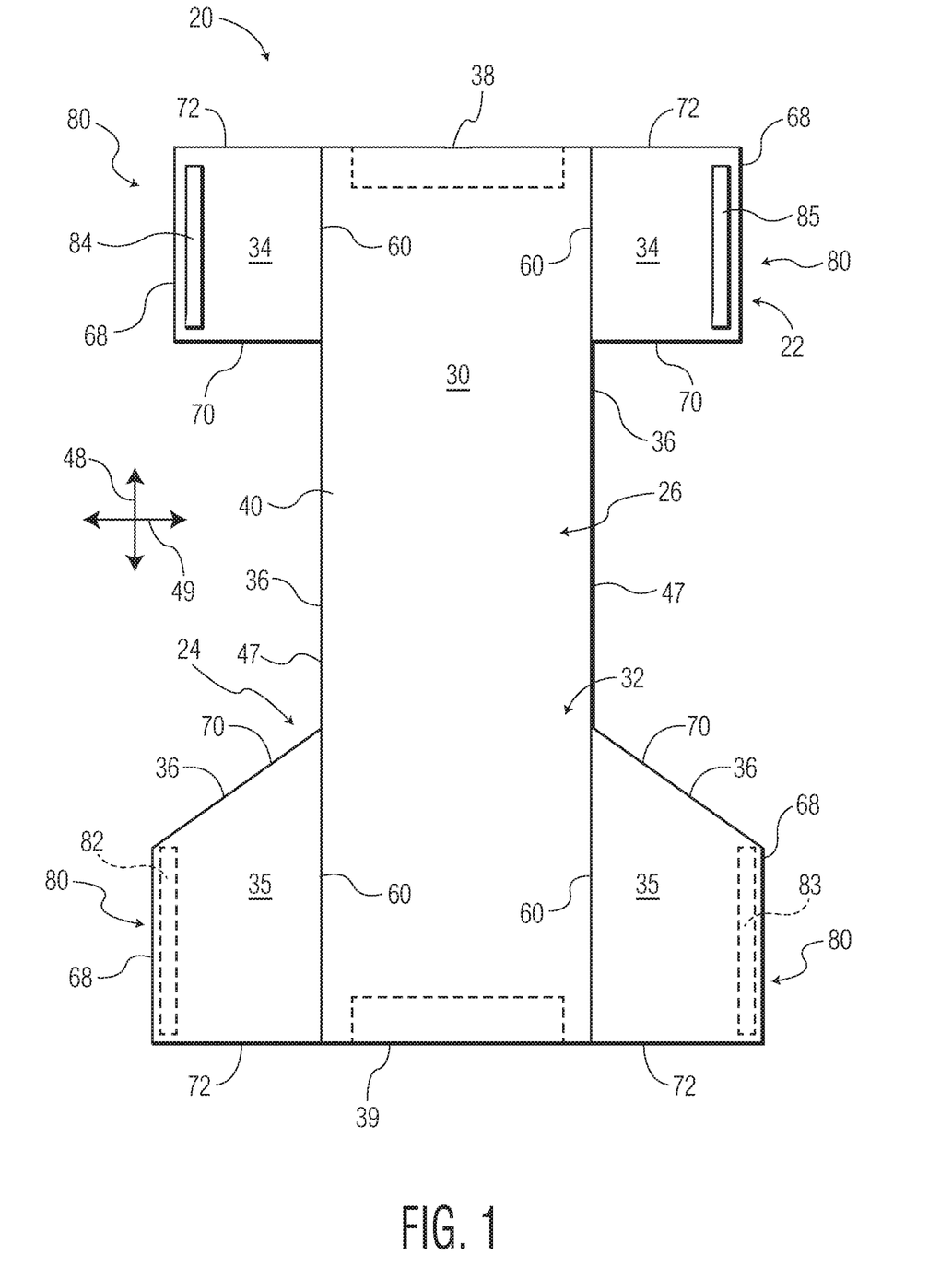
FIG. 1 is a bottom plan view of one embodiment of an absorbent article in the form of training pants in an unfastened, unfolded, and laid flat condition, and showing the outer cover to the viewer.
Figure 2:
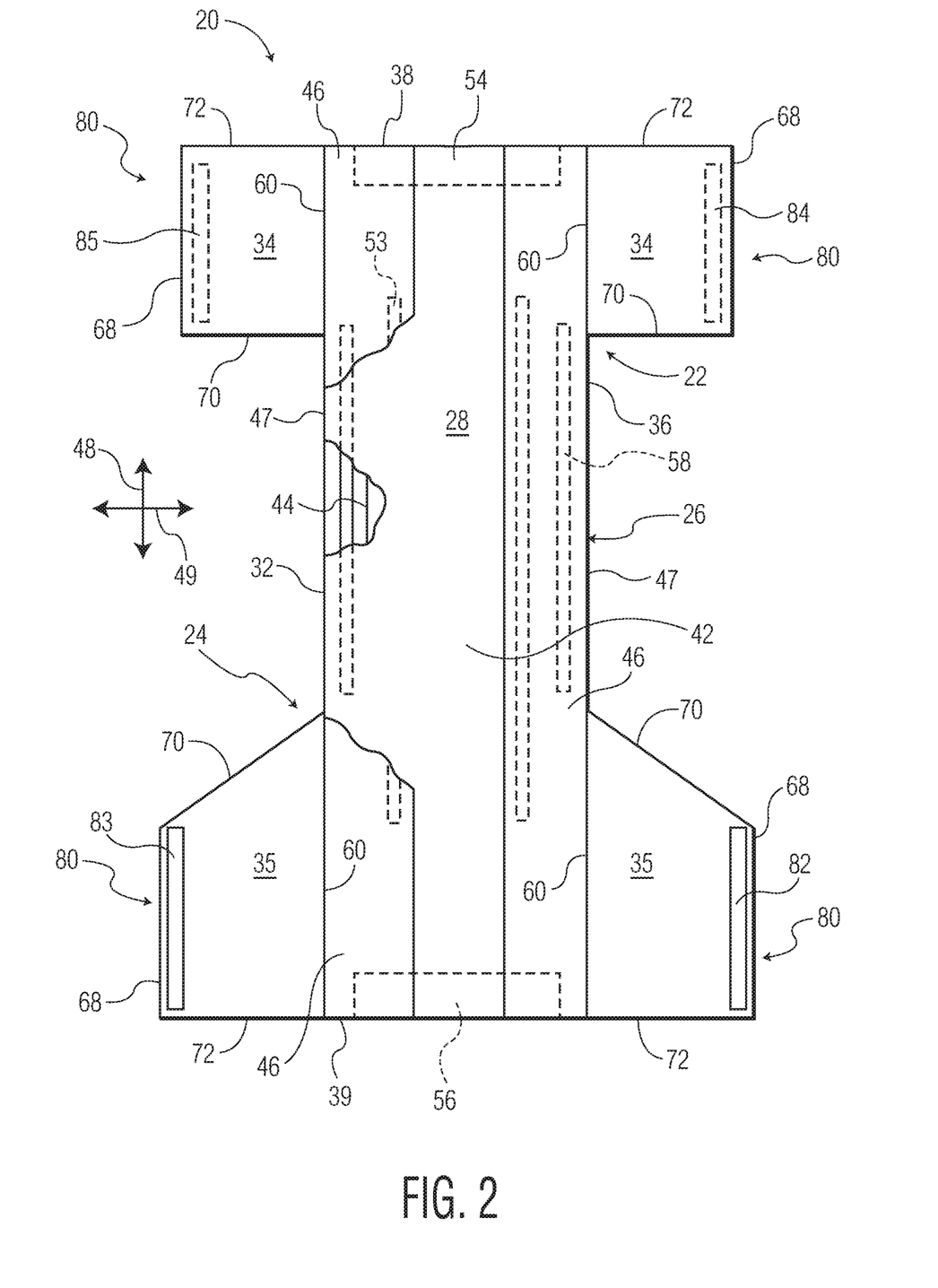
FIG. 2 is a top plan view of the absorbent article of FIG. 1 showing the bodyside liner to the viewer and with portions cut away to show underlying features.

The term "cross direction assembly" refers herein to a process in which disposable absorbent products are manufactured in an orientation in which the products are connected side-to-side, e.g., in the transverse direction shown by arrow 49 in FIGS. 1 and 2. A process utilizing cross direction assembly entails products traveling through a converting machine parallel to the direction of arrow 49, as opposed to "machine direction assembly" in which the products are connected end-to-end or waist-to-waist.

The terms "elastic," "elasticized" and "elasticity" mean that property of a material or composite by virtue of which it tends to recover its original size and shape after removal of a force causing a deformation.

The term "fabrics" refers herein to any woven, knitted and nonwoven fibrous webs.

The term "film" refers herein to a thermoplastic film made using an extrusion and/or forming process, such as a cast film or blown film extrusion process. The term includes apertured films, slit films, and other porous films that constitute liquid transfer films, as well as films that do not transfer fluids, such as, but not limited to, barrier films, filled films, breathable films, and oriented films.

The term "hydrophilic" refers herein to fibers or the surfaces of fibers which are wetted by aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by Cahn SFA-222 Surface Force Analyzer System, or a substantially equivalent system. When measured with this system, fibers having contact angles less than 90 are designated "wettable" or hydrophilic, while fibers having contact angles greater than 90 are designated "nonwettable" or hydrophobic.

The term "liquid impermeable" refers herein to a layer or multi-layer laminate in which liquid body exudates, such as urine, will not pass through the layer or laminate, under ordinary use conditions, in a direction generally perpendicular to the plane of the layer or laminate at the point of liquid contact.

The term "liquid permeable" refers herein to any material that is not liquid impermeable.

The terms "longitudinal" and "transverse" have their customary meaning, as indicated by the longitudinal and transverse axes depicted in FIGS. 1 and 2. The longitudinal axis lies in the plane of the article and is generally parallel to a vertical plane that bisects a standing wearer into left and right body halves when the article is worn. The transverse axis lies in the plane of the article generally perpendicular to the longitudinal axis. The article as illustrated is longer in the longitudinal direction than in the transverse direction.

The term "machine direction" refers herein to the length of a fabric in the direction in which it is produced, as opposed to "cross direction" that refers to the width of a fabric in a direction generally perpendicular to the machine direction.

The term "machine direction assembly" refers herein to a process in which disposable absorbent products are manufactured in an orientation in which the products are connected end-to-end or waist-to-waist, in the longitudinal direction shown by arrow 48 in FIGS. 1 and 2, a process utilizing a machine direction assembly entails products traveling through a converting machine parallel to the direction of arrow 48, as opposed to "cross direction assembly" in which the products are connected side-to-side.

The term "meltblown" refers herein to fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which can be to microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin et al., which is incorporated herein by reference. Meltblown fibers are microfibers which may be continuous or discontinuous, are generally smaller than about 0.6 denier, and may be tacky and self-bonding when deposited onto a collecting surface.

The term "nonwoven" refers herein to a material which is formed without the aid of a textile weaving or knitting process. The material can have a structure of individual fibers, filaments, or threads (collectively referred to as "fibers") which can be interlaid, but not in an identifiable manner as in a knitted fabric. Nonwoven material can be formed from many processes such as, but not limited to, meltblowing processes, spunbonding processes, carded web processes, etc.

The term "operatively joined," in reference to the attachment of an elastic member to another element, means that the elastic member when attached to or connected to the element, or treated with heat or chemicals, by stretching, or the like, gives the element elastic properties; and with reference to the attachment of a non-elastic member to another element, means that the member and element can be attached in any suitable manner that permits or allows them to perform the intended or described function of the joinder. The joining, attaching, connecting or the like can be either directly, such as joining either member directly to an element, or can be indirectly by means of another member disposed between the first member and the first element.

The term "refastenable" refers herein to the property of two elements being capable of releasable attachment, separation, and subsequent releasable reattachment without substantial permanent deformation or rupture.

The terms "releasably attached," "releasably engaged," and variations thereof refer herein to two elements being connected or connectable such that the elements tend to remain connected absent a separation force applied to one or both of the elements, and the elements being capable of separation without substantial permanent deformation or rupture. The required separation force is typically beyond that encountered while wearing the absorbent garment. It should be noted that a releasably attached or releasably engaged seam is a refastenable seam that does not include a bonded seam that must be torn, cut, or otherwise disrupted.

The term "spunbond" refers herein to small diameter fibers that are formed by extruding molten thermoplastic material as filaments from a plurality of fine capillaries of a spinnerette having a circular or other configuration, with the diameter of the extruded filaments then being rapidly reduced by a conventional process such as, for example, eductive drawing, and processes that are described in U.S. Pat. No. 4,340,563 to Appel et al., U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Petersen, and U.S. Pat. No. 3,542,615 to Dobo et al., each of which is incorporated herein in its entirety by reference. Spunbond fibers are generally continuous and often have average deniers larger than about 0.3, and in an embodiment, between about 0.6, 5, and 10 and about 15, 20 and 40. Spunbond fibers are generally not tacky when they are deposited on a collecting surface.

The term "stretchable" refers herein that a material can be stretched, without breaking, to at least 150% of its initial (unstretched) length in at least one direction, suitably to at least 200% of its initial length, desirably to at least 250% of its initial length.

Figure 3:
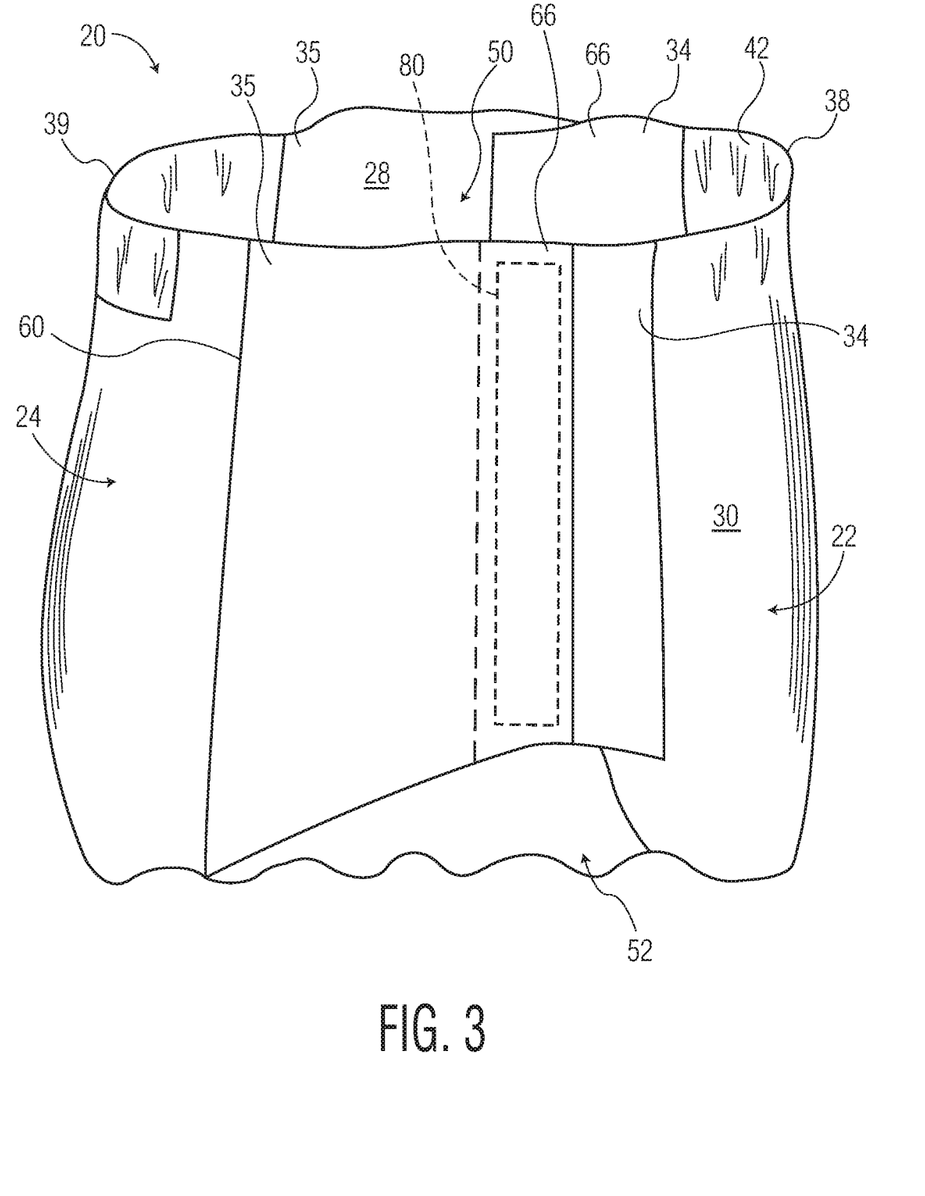
FIG. 3 is a partial schematic view of the absorbent article of FIGS. 1 and 2.

Absorbent Article:

Referring to FIGS. 1-3, an absorbent article 20 according to one embodiment is illustrated in the form of a pants-type absorbent article for wear about a wearer's waist, and more particularly in the form of children's toilet training pants. FIGS. 1 and 2 provide illustrations of the absorbent article 20 in an unfastened, unfolded and laid flat configuration with either the outer cover 40 facing the viewer (FIG. 1) or the bodyside liner 42 facing the viewer (FIG. 2). FIG. 3 provides a partial schematic illustration of the absorbent article 20 of FIGS. 1 and 2 in a fully assembled configuration (broadly referred to herein as a wear configuration of the absorbent article 20). The absorbent article 20 can be placed against or in proximity to the body of the wearer to absorb and/or retain various bodily exudates discharged from the body. The absorbent article 20 can be disposable and, therefore, can be discarded after a limited period of use instead of being laundered or otherwise restored for reuse. It is understood that the concepts described herein are suitable for use with various other pants-type absorbent articles such as adult incontinence articles, as well as other articles intended for personal wear such as clothing, diapers, feminine hygiene products, medical garments, surgical pads and bandages, other personal care or health care garments, and the like without departing from the scope of the present disclosure.

By way of illustration only, various materials and methods for constructing the absorbent article 20 are disclosed in PCT Patent Application WO 00/37009 published Jun. 29, 2000 by A. Fletcher et al; U.S. Pat. No. 4,940,464 issued Jul. 10, 1990 to Van Gompel et al.; and U.S. Pat. No. 5,766,389 issued Jun. 16, 1998 to Brandon et al., each of which are incorporated herein by reference to the extent they do not conflict with the disclosure herein.

The absorbent article 20 can have a longitudinal direction 48 and a transverse direction 49. The absorbent article 20 includes a front waist region 22, a back waist region 24, a crotch region 26 extending longitudinally between and interconnecting the front waist region 22 and back waist region 24 along a longitudinal direction of the absorbent article 20, an inner surface 28 configured for contiguous relationship with the wearer, and an outer surface 30 opposite the inner surface 28. The absorbent article 20 also has a pair of laterally opposite side edges 36 and a pair of longitudinally opposite waist edges, respectively designated front waist edge 38 and back waist edge 39. The front waist region 22 is contiguous with the front waist edge 38, and the back waist region 24 is contiguous with the back waist edge 39.

The absorbent article 20 includes a central absorbent assembly 32, which when laid flat as in FIGS. 1 and 2 can be rectangular or any other desired shape. A pair of laterally opposite front side panels 34 extends outward from the absorbent assembly 32 at the front waist region 22 (thereby forming transversely outer portions of the front waist region 22, and more broadly in part forming transversely opposite sides of the absorbent article 20). Laterally opposite back side panels 35 extend outward from the absorbent assembly 32 at the back waist region 24 (thereby forming transversely outer portions of the back waist region 24, and together with the front side panels 34 further defining the sides of the absorbent article 20). While the absorbent article 20 is illustrated as having a pair of front side panels 34 and a pair of back side panels 35, in various embodiments, the absorbent article 20 can have only a pair of back side panels 35 which can have a width dimension in the transverse direction 49 such that each of the back side panels 35 can be bonded to the front waist region 22 of the absorbent article 20 and can define the sides of the absorbent article 20. In various embodiments, the absorbent article 20 may not have separately attached side panels but may have integral extensions of the outer cover 40 and/or the bodyside liner 42 such as, for example, in the back waist region 24 which can extend in the transverse direction 49 such that they can be bonded to the front waist region 22 of the absorbent article 20 and can define the sides of the absorbent article 20.

The central absorbent assembly 32 of the absorbent article 20 includes an outer cover 40 and a bodyside liner 42 in a superimposed relationship with the outer cover 40 and bonded to the outer cover 40 by suitable means such as adhesives, ultrasonic bonds, thermal bonds or other conventional techniques. An absorbent structure 44 is disposed between the outer cover 40 and the bodyside liner 42. A pair of containment flaps 46 is bonded to the bodyside liner 42 for inhibiting the lateral flow of body exudates. The central absorbent assembly 32 has opposite ends that form portions of the front and back waist edges 38 and 39, and opposite side edges 47 that form portions of the side edges 36 of the absorbent article 20.

The absorbent assembly 32 and side panels (34 and 35) can include two or more separate elements or they can be integrally formed with the absorbent article 20. Integrally formed side panels (34 and 35) and absorbent assembly 32 would include at least some common materials, such as the bodyside liner 42, flap composite 46, outer cover 40, other materials and/or combinations thereof, and could define a one-piece elastic, stretchable, or nonstretchable absorbent article 20.

The front waist region 22 of the absorbent article 20 can be selectively joined to the back waist region 24 of the absorbent article 20 via a pair of refastenable side seams 66 to define, in the illustrated embodiment, a pull-on, pant-like configuration of the absorbent article 20 having a waist opening 50 and leg openings 52. Each side seam 66 can be formed from a fastening system 80. The fastening system 80 may include any suitable complementary refastenable fasteners including, for example and without limitation, hook- and loop-type fasteners, other types of mechanical fasteners, adhesive fasteners, cohesive fasteners, and combinations thereof. In some suitable embodiments, the fastening system 80 may be fastened during the manufacturing process of the absorbent article 20 such that the absorbent article 20 is supplied to the wearer in a fastened configuration. While FIG. 3 illustrates the front waist region 22 and back waist region 24 being joined together via refastenable side seams 66, it is understood that the front waist region 22 and back waist region 24 can be joined together via non-refastenable, bonded seams (e.g., by adhesive bonding, ultrasonic bonding, pressure bonding, thermal bonding).

With the absorbent article 20 in the fastened condition as illustrated in FIG. 3, the front side panels 34 and back side panels 35 are releasably attached to each other by a fastening system 80 to define the assembled three-dimensional wear configuration of the absorbent article 20 having a waist opening 50 and a pair of leg openings 52. The front waist region 22 includes the portion of the absorbent article 20 that, when worn, is positioned at least in part on the front of the wearer while the back waist region 24 includes the portion of the absorbent article 20 that is positioned at least in part on the back of the wearer. The crotch region 26 of the absorbent article 20 includes the portion of the absorbent article 20 that is positioned between the legs of the wearer and covers the lower torso of the wearer. In embodiments in which the absorbent article 20 has only a pair of transversely extending back side panels 35, whether integral or separately attached, a fastener component of the fastening system 80 can be positioned on the back side panels 35 and the complementary fastener can be positioned on the outer cover 40 of the front waist region 22.

The front side panels 34 and back side panels 35 include portions of the absorbent article 20 (and more particularly of the front waist region 22 and back waist region 24) that, when worn, are positioned on the hips of the wearer. The side panels (34 and 35) thus broadly define the transversely opposite sides of the absorbent article 20 at a refastenable seam 66 along which the fastening system 80 releasably attaches the front side panels 34 and back side panels 35. The waist edges 38 and 39 of the absorbent article 20 are configured to encircle the waist of the wearer and together define the waist opening 50. Portions of the side edges 36 in the crotch region 26 generally define leg openings 52. The side panels (34 and 35) can have a panel length dimension measured parallel to the longitudinal axis 48 along the outer edge 68 of each side panel (34 and 35). In various embodiments, the panel length dimension of the back side panel 35 is longer than the panel length dimension of the front side panel 34.

The central absorbent assembly 32 is configured to contain and/or absorb exudates discharged from the wearer. For example, the containment flaps 46 are configured to provide a barrier to the transverse flow of body exudates. A flap elastic member 53 can be operatively joined with each containment flap 46 in any suitable manner as is well known in the art. The elasticized containment flaps 46 define a partially unattached edge that assumes an upright configuration in at least the crotch region 26 of the absorbent article 20 to form a seal against the wearer's body. The containment flaps 46 can be located along the side edges 36 of the absorbent article 20, and can extend longitudinally along the entire length of the absorbent assembly 32 or can only extend partially along the length of the absorbent assembly 32. Suitable constructions and arrangements for the containment flaps 46 are generally well known to those skilled in the art and are described in U.S. Pat. No. 4,704,116 issued Nov. 3, 1987 to Enloe, which is incorporated herein by reference.

To further enhance containment and/or absorption of body exudates, the absorbent article 20 also suitably includes a front waist elastic member 54, a rear waist elastic member 56, and leg elastic members 58, as are known to those skilled in the art. The waist elastic members (54 and 56) can be attached to the outer cover 40 and/or the bodyside liner 42 along the opposite waist edges (38 and 39), and can extend over part or all of the waist edges (38 and 39). The leg elastic members 58 can be attached to the outer cover 40 and/or the bodyside liner 42 along the opposite side edges 36 and positioned in the crotch region 26 of the absorbent article 20. The leg elastic members 58 can be longitudinally aligned along each side edge 47 of the absorbent assembly 32.

The outer cover 40 suitably includes a material that is substantially liquid impermeable. The outer cover 40 can be a single layer of liquid impermeable material, but more suitably includes a multi-layered laminate structure in which at least one of the layers is liquid impermeable. The inner layer of the outer cover 40 can be both liquid and vapor impermeable, or it can be liquid impermeable and vapor permeable. It is also contemplated that the outer cover 40 can be stretchable, and more suitably elastic. In particular, the outer cover 40 is suitably stretchable and more suitably elastic in at least the transverse direction of the absorbent article 20. In other aspects the outer cover 40 can be stretchable, and more suitably elastic, in both the transverse direction 49 and the longitudinal direction 48.

The liquid permeable bodyside liner 42 is illustrated as overlying the outer cover 40 and absorbent structure 44, and can, but need not, have the same dimensions as the outer cover 40. The bodyside liner 42 is suitably compliant, soft feeling, and non-irritating to the wearer's skin. Further, the bodyside liner 42 can be less hydrophilic than the absorbent structure 44 to present a relatively dry surface to the wearer and permit liquid to readily penetrate through its thickness. Alternatively, the bodyside liner 42 can be more hydrophilic or can have essentially the same affinity for moisture as the absorbent structure 44 to present a relatively wet surface to the wearer to increase the sensation of being wet. This wet sensation can be useful as a training aid. The hydrophilic/hydrophobic properties can be varied across the length, width and/or depth of the bodyside liner 42 and absorbent structure 44 to achieve the desired wetness sensation or leakage performance. The bodyside liner 42 can also be stretchable, and more suitably elastic. In particular, the bodyside liner 42 is suitably stretchable and more suitably elastic in at least the transverse direction 49 of the absorbent article 20. In other aspects, the bodyside liner 42 can be stretchable, and more suitably elastic, in both the transverse direction 49 and the longitudinal direction 48.

As noted previously, the illustrated absorbent article 20 has front side panels 34 and back side panels 35 defining transversely opposite sides of the absorbent article 20 in the wear configuration of the absorbent article 20. The side panels (34 and 35) can be bonded along seams 60 to the central absorbent assembly 32 in the respective front waist region 22 and back waist region 24. In various embodiments, the front side panels 34 can be bonded to and extend transversely outward beyond the side edges 47 of the absorbent assembly 32 in the front waist region 22 and the back side panels 35 can be bonded to and extend transversely outward beyond the side edges 47 of the absorbent assembly 32 in the back waist region 24. The side panels (34 and 35) can be bonded to the absorbent assembly 32 using bonding means known to those skilled in the art such as adhesive, thermal, pressure or ultrasonic bonding. Alternatively, the side panels (34 and 35) can be formed as an integral portion of a component of the absorbent assembly 32. For example, the side panels (34 and 35) can include a generally wider portion of and be an extension of the outer cover 40, the bodyside liner 42, and/or another component of the absorbent assembly 32.

The front side panels 34 and back side panels 35 each have an outer edge 68 spaced transversely from the side seam 66, a leg end edge 70 disposed toward the longitudinal center of the absorbent article 20, and a waist end edge 72 disposed toward a longitudinal end of the absorbent article 20. The leg end edge 70 and waist end edge 72 extend from the side edges 47 of the absorbent assembly 32 to the outer edges 68. The leg end edges 70 of the side panels (34 and 35) form part of the side edges 36 of the absorbent article 20. In various embodiments, the leg end edges 70 can be curved and/or angled relative to the transverse axis 49 to provide a better fit around the wearer's legs. However, it is understood that only one or both of the leg end edges 70 can be curved or angled, such as the leg end edge 70 of the back waist region 24, or neither of the leg end edges 70 can be curved or angled, without departing from the scope of this disclosure. The waist end edges 72 are suitably parallel to the transverse axis 49. The waist end edges 72 of the front side panels 34 form part of the front waist edge 38 of the absorbent article 20, and the waist end edges 72 of the back side panels 35 form part of the back waist edge 39 of the absorbent article 20.

The side panels (34 and 35) can have a panel width dimension measured parallel to the transverse axis 49. The panel width dimension can be measured as the width in the transverse direction 49 between the outer edge 68 of each side panel (34 and 35) and the seam 60 between each panel (34 and 35) and the central absorbent assembly 32. In various embodiments, the panel width dimension of the back side panel 35 is wider than the panel width dimension of the front side panel 34.

The side panels (34 and 35) suitably, although not necessarily, include a stretchable material capable of stretching in a direction generally parallel to the transverse axis 49 of the absorbent article 20. More suitably the side panels (34 and 35) include an elastic material. Suitable elastic materials, as well as one process of incorporating stretchable side panels into absorbent articles 20, are described in the following U.S. Pat. No. 4,940,464 issued Jul. 10, 1990 to Van Gompel et al.; U.S. Pat. No. 5,224,405 issued Jul. 6, 1993 to Pohjola; U.S. Pat. No. 5,104,116 issued Apr. 14, 1992 to Pohjola; and U.S. Pat. No. 5,046,272 issued Sep. 10, 1991 to Vogt et al.; all of which are incorporated herein by reference. Optionally, the stretch material can include a stretch-thermal laminate (STL), a neck-bonded laminate (NBL), a reversibly necked laminate, or a stretch-bonded laminate (SBL) material. Methods of making such materials are well known to those skilled in the art and described in U.S. Pat. No. 4,663,220 issued May 5, 1987 to Wisneski et al.; U.S. Pat. No. 5,226,992 issued Jul. 13, 1993 to Morman; and PCT application WO 01/88245 in the name of Welch et al.; all of which are incorporated herein by reference. Other suitable materials are described in U.S. patent application Ser. No. 12/649,508 to Welch et al. and U.S. Pat. No. 8,287,677 to Lake et al., all of which are incorporated herein by reference. Alternatively, the side panel material can include other woven or nonwoven materials, such as those described above as being suitable for the outer cover 40 or bodyside liner 42; mechanically pre-strained composites; or stretchable but inelastic materials.

The absorbent article 20 includes a fastening system 80 for refastenably securing the absorbent article 20 about the waist of the wearer. The fastening system 80 includes first fastening components (82 and 83) that are adapted to refastenably connect to mating second fastening components (84 and 85). In an embodiment, one surface of each of the first fastening components (82 and 83) can have a plurality of engaging elements that project from that surface. The engaging elements of the first fastening components (82 and 83) are adapted to repeatedly engage and disengage engaging elements of the second fastening components (84 and 85).

In an embodiment, the first fastening components (82 and 83) each have hook type fasteners and the second fastening components (84 and 85) each have complementary loop type fasteners. In another embodiment, the first fastening components (82 and 83) each have loop type fasteners and the second fastening components (84 and 85) each have complementary hook type fasteners. Alternatively, the fastening components can be interlocking similar surface fasteners; adhesive or cohesive fastening elements such as an adhesive fastener and an adhesive-receptive landing zone or material; or the like.

Loop type fasteners can be a fabric or material having a base or backing structure and a plurality of loop members extending upwardly from at least one surface of the backing structure. The loop material can be formed of any suitable material, such as acrylic, nylon, polypropylene or polyester, and can be formed by methods such as warp knitting, stitch bonding, or needle punching. Loop type materials can also comprise any fibrous structure capable of entangling or catching hook type materials, such as carded, spunbond, or other nonwoven webs or composites, including elastomeric and nonelastomeric composites.

Hook type fasteners can be a fabric or material having a base or backing structure and a plurality of hook members extending upwardly from at least one surface of the backing structure. In contrast to the loop type fasteners which can be flexible fabric, the hook material can be a resilient material to minimize unintentional disengagement of the fastener component as a result of the hook material becoming deformed and catching on clothing or other items. The term "resilient" refers to an interlocking material having a predetermined shape and the property of the interlocking material to resume the predetermined shape after being engaged and disengaged from a mating, complementary interlocking material. Suitable hook material can be molded or extruded of nylon, polypropylene, or another suitable material. Suitable hook materials area available from commercial vendors such as Velcro Industries and Minnesota Mining & Manufacturing Co.

The first fastening components (82 and 83) can be positioned at the body facing surface of the absorbent article 20 in the back waist region 24. The first fastening components (82 and 83) can be positioned along the outer edges 68 of the back side panels 35. In various embodiments, the first fastening components (82 and 83) can be positioned proximate to the waist end edge 72. The second fastening components (84 and 85) can be positioned on the garment facing surface of the absorbent article 20 in the front waist region 22. The second fastening components (84 and 85) are sized to receive the first fastening components (82 and 83) and can be positioned along the outer edges 68 of the front side panels 34. In various embodiments in which the absorbent article 20 does not have front side panels 34, the second fastening components (84 and 85) can be positioned on the outer cover 40 of the absorbent article 20 in the front waist region 22 of the absorbent article 20. In various embodiments, the second fastening components (84 and 85) can be positioned proximate to the waist end edge 72. In various embodiments, the first fastening components (82 and 83) can be a loop type fastener and the second fastening component (84 and 85) can be a complementary hook type fastener.

The fastening components (82, 83, 84 and 85) can be bonded to the side panels (34 and 35) by any means known to those skilled in the art such as adhesive bonds, ultrasonic bonds or thermal bonds. The fastening components (82, 83, 84 and 85) can be separate fastening elements or can be distinct region of an integral material with the absorbent article 20. For example, the absorbent article 20 can include an integral second fastening material disposed in the front waist region 22 which define the second fastening components (84 and 85). In various embodiments, for example, a front side panel 34 or a back side panel 35 can have a material which is releasably engageable with fastening components located in the opposite waist region.

When connected, the fastening components (82, 83, 84 and 85) form refastenable side seams 66. In various embodiments, the refastenable side seams 66 can extend substantially the entire distance between the waist opening 50 and the leg openings 52. In various embodiments, the refastenable side seams 66 can extend from 80 or 90 percent to 98 or 100 percent of the distance between the waist opening 50 and the leg openings 52, which distance is measured parallel to the longitudinal axis 48.

In various embodiments, the refastenable side seams 66 are positioned closer to the front of the wearer rather than the back or the sides of the wearer. The side panels (34 and 35) can have a panel width dimension measured parallel to the transverse axis 49. The panel width dimension can be measured as the width in the transverse direction 49 between the outer edge 68 of each side panel (34 and 35) and the seam 60 between each panel (34 and 35) and the central absorbent assembly 32. In various embodiments, the panel width dimension of the back side panel 35 is wider than the panel width dimension of the front side panel 34. In such embodiments, the outer edge 68 of the back side panels 35 is located a distance further away from the absorbent assembly 32 in the transverse direction than the outer edge 68 of the front side panels 34. In various embodiments, the panel width dimension of the front side panel 34 is wider than the panel width dimension of the back side panel 35. In such embodiments, the outer edge 68 of the front side panels 34 is located a distance further away from the absorbent assembly 32 in the transverse direction than the outer edge 68 of the back side panels 35.

The various components of the absorbent article 20 can be bonded together by any means known to those skilled in the art such as, for example, adhesive, thermal and/or ultrasonic bonds. Suitable absorbent supply mechanisms, web unwinds, conveyor systems, registration systems, drive systems, control systems, and the like, for use in the manufacture of the absorbent article 20 are disclosed in U.S. Pat. No. 5,766,389 to Brandon et al. which is incorporated herein by reference to the extent it does not conflict with the disclosure herein. Many manufacturing processes to make an absorbent article 20 generally produce a continuous web of interconnected absorbent articles 20. The continuous web of interconnected absorbent articles 20 can pass through a cutter which can selectively cut the continuous web of interconnected absorbent articles 20 into discrete absorbent articles 20. Such cutters are generally known to those skilled in the art and can include, for example, the combination of a cutting roll and an anvil roll through which the continuous web of interconnected absorbent articles 20 can pass. Following the cutting of the continuous web of interconnected absorbent articles 20 into discrete absorbent articles 20, the discrete absorbent article 20 can then be folded using any suitable folding mechanism. The absorbent article 20 can be folded about a fold line generally bisecting the absorbent article 20. The fold line extends in a transverse direction through the crotch region 26 of the absorbent article 20. As such, the waist regions, 22 and 24, of the absorbent article 20 are positioned in a facing relationship and the side panels, 34 and 35, extend transversely outward relative to the longitudinal axis 48 of the absorbent article 20.

A variety of folding mechanisms can be used, such as, but not limited to, blade folders, linear folders, book folders, tucker blades, and the like. The specific type selected for a given application may depend upon the type of absorbent article 20 being manufactured and the type of fastening system used to secure the absorbent article 20 in a wear configuration. During the folding process, the side panels, 34 and 35, should be controlled so that the refastenable fastening components, 82, 83, 84 and 85, are unlikely to engage one another or engage another material of the absorbent article 20 during the folding operation.

In an embodiment, a folding mechanism can be a blade folding mechanism which can have a plurality of rotating folding or tucker blades which can be configured to contact the absorbent article 20 along the fold line. Rotation of the folding blades can force the absorbent article 20 into a nip between two rotating folding conveyors which can cause the absorbent article 20 to fold about the fold line. The folding conveyors can form part of a transport system for moving the folded absorbent article 20 in the machine direction 104. The folded absorbent article 20 can be moved in the machine direction 104 through the process with the crotch region 26 leading the waist regions, 22 and 24. In various embodiments, the waist regions, 22 and 24, can lead the crotch region 26.

Figure 4:
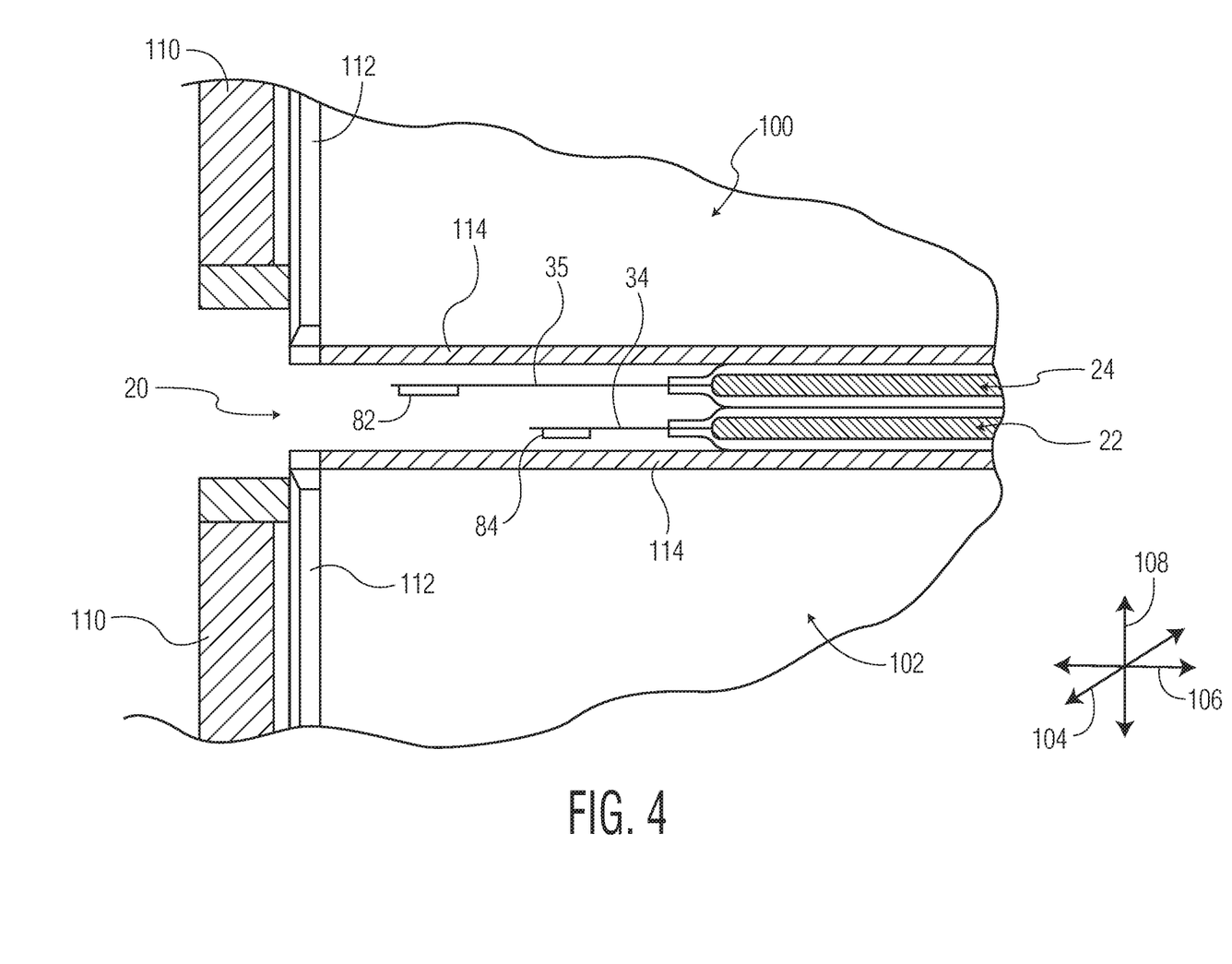
FIG. 4 is an enlarged section view of a portion of a folded absorbent article.

FIG. 4 illustrates a portion of a folded absorbent article 20 positioned between and upper folding conveyor 100 and a lower folding conveyor 102. At this point in a manufacturing process for the absorbent article 20, the absorbent article 20 has been folded in half and is being transported in the machine direction 104 by each of the upper folding conveyor 100 and lower folding conveyor 102. In various embodiments, each of the upper folding conveyor 100 and the lower folding conveyor 102 can have a frame structure 110, a plurality of rotatable pulleys 112 associated with the frame structure 110, and a continuous belt 114 carried on the pulleys 112. A drive system and a conveyor shaft can be used to drive one or more of the pulleys 112. The upper folding conveyor 100 and the lower folding conveyor 102 can be vacuum conveyors in which case the continuous belt 114 can be formed of a fluid permeable material, such as one having holes. The upper folding conveyor 100 and the lower folding conveyor 102 can transport the absorbent article 20 with the longitudinal center line of the absorbent article 20 traveling on the longitudinal center line of the upper folding conveyor 100 and the lower folding conveyor 102. The front side panels 34 and the back side panels 35 can project in a transverse direction 49 outward from the frame structure 110 in the cross direction 106.

As a result of the folding of the absorbent article 20, the front waist region 22 and the front side panels 34 are disposed above the back waist region 24 and the back side panels 35 in the z-direction 108. The first fastening component, 82 and 83, is disposed on the body facing surface of the absorbent article 20 in the back waist region 24 and the second fastening component, 84 and 85, is disposed on the garment facing surface of the absorbent article 20 in the front waist region 22.

While traveling on the upper folding conveyor 100 and the lower folding conveyor 102, the side panels, 34 and 35, can be smoothed out or straightened if desired by various means including fluid stabilizing devices. Such fluid stabilizing devices can include air knives, air bars, air nozzles, vacuum nozzles, or the like to provide a stream of fluid directed toward or away from the side panels, 34 and 35. The fluid stabilizing devices can be incorporated within either or both of the upper folding conveyor 100 and lower folding conveyor 102 or can be separate devices positioned in proximity to the conveyors. Other suitable mechanisms for smoothing and straightening the side panels, 34 and 35, are disclosed in U.S. Pat. No. 5,046,272 to Vogt et al., which is incorporated herein by reference to the extent not in conflict with the disclosure herein.

Figure 5:
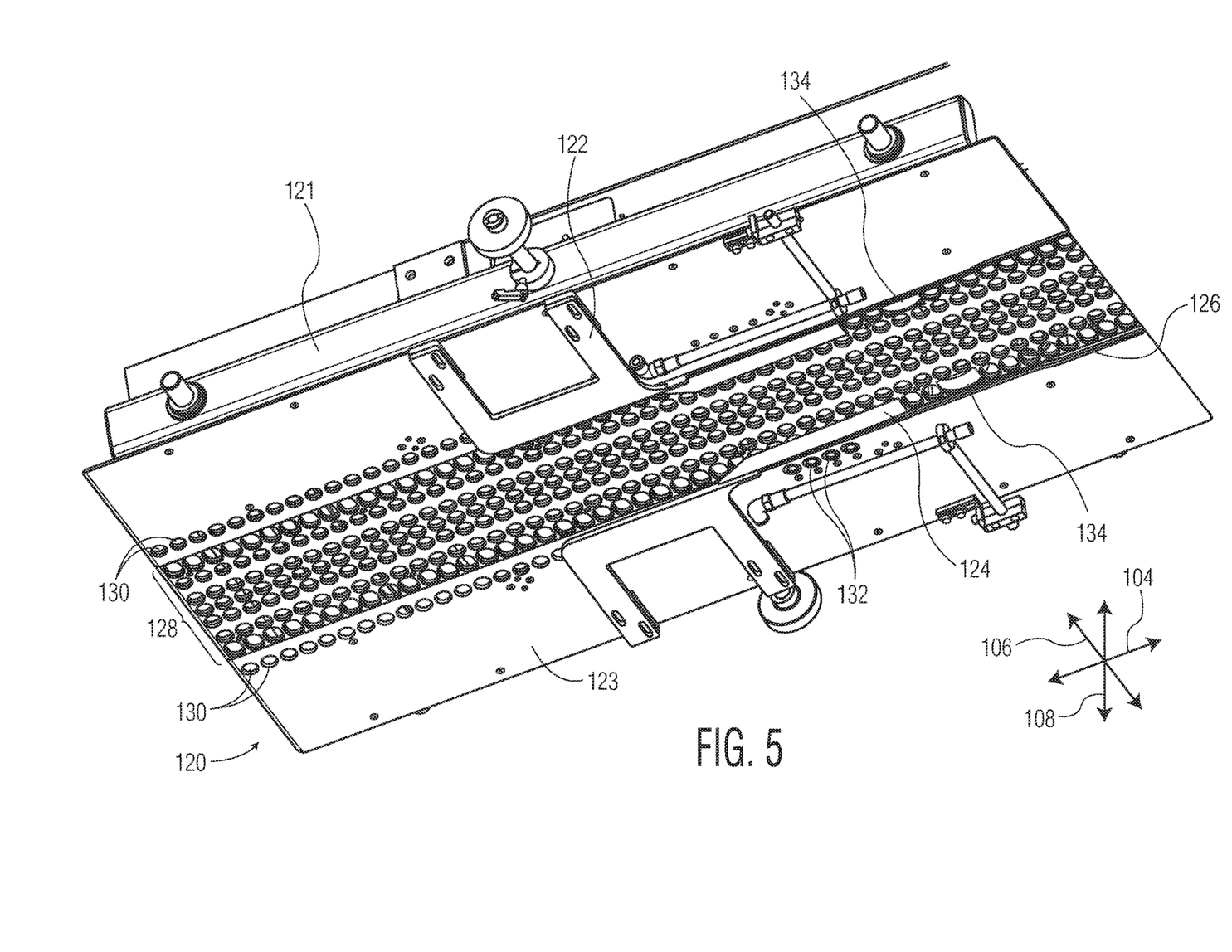
FIG. 5 is an isometric view of an upper folding conveyor.

The front side panels 34 can be refastenably engaged with the back side panels 35 in a seaming section of a manufacturing process. The seaming section can include processes and apparatus for controlling the unattached side panels, 34 and 35, folding the wider of the side panels, 34 or 35, and bonding the opposing fastening components to each other to form the refastenable side seams 66. The folded absorbent article 20 can be transported through the seaming section by a transport system, such as conveyors. In various embodiments, the absorbent article 20 is transferred from the upper folding conveyor 100 and lower folding conveyor 102 to an upper fastening conveyor 120 (such as illustrated in FIG. 5) and a lower fastening conveyor. As illustrated in FIG. 5, the upper fastening conveyor 120 can have a frame structure 121, one or more vacuum chambers defined within the frame structure 121, and one or more continuous fluid-permeable belts 123 carried on a plurality of rotatable pulleys or other suitable devices. A drive system and conveyor shaft can be used to rotatively drive one or more of the pulleys. The vacuum chambers can be operatively connected to a source of vacuum and the belt 123 can be provided with a plurality of a primary arrangement of holes 128. The belt 123 of the upper fastening conveyor 120 can further have a plurality of a secondary arrange of holes 130. The primary arrangement of holes 128 can maintain the body of the absorbent article 20 in position on the upper fastening conveyor 120 and the secondary arrangement of holes 130 can maintain the side panels, 34 and 35, in position on the upper fastening conveyor 120. A lower fastening conveyor can operatively associate with the upper fastening conveyor 120 in the transport of the absorbent article 20 through the manufacturing process. A lower fastening conveyor can assist in maintaining the positioning of the absorbent article 20 on the upper fastening conveyor 120 and can also have a frame structure and one or more continuous belts carried on a plurality of rotatable pulleys or other suitable devices. The lower fastening conveyor can be relatively narrow compared to the upper fastening conveyor 120 and can have a width, for example, equal to the width of the chassis of the absorbent article 20. Such a width permits the side panels, 34 and 35, which are positioned on the upper fastening conveyor 120, to extend in the cross-direction 106 beyond the lower fastening conveyor. In various embodiments, the width of the lower fastening conveyor can correspond to the width between the seams 60 which bond the side panels 34 and 35 to the absorbent assembly 32.

The upper fastening conveyor 120 can further include an alignment plate 122 which can align the side panels, 34 and 35, into close proximity with each other prior to the folding of the wider side panel, 34 or 35, over the side panel of the smaller width dimension. The upper fastening conveyor 120 can include a fold plate 124. In various embodiments, the fold plate 124 can be an extension of the alignment plate 122. In various embodiments, the fold plate 124 can be a component separate from the alignment plate 122. In various embodiments, the width of the fold plate 124 in the cross-direction 106 can be narrower than the width dimension of the alignment plate 122 in the cross-direction. Compressed air openings 132 can be positioned adjacent to the fold plate 124 in the cross-direction of the upper fastening conveyor 120. The compressed air openings 132 can be connected to a source of compressed air. The upper fastening conveyor 120 can have at least one pair of engagement rollers 134. Each engagement roller 134 of the pair can be positioned on opposing sides in the machine direction 104 of the primary arrangement of holes 128. The upper fastening conveyor 120 can also have a pair of engagement rods 126. Each engagement rod 126 can be positioned on opposing sides in the machine direction 104 of the primary arrangement of holes 128. The pair of engagement rods 126 can be positioned downstream of the engagement rollers 134.

In various embodiments, in the formation of the refastenable side seams 66 of the absorbent article 20, the second fastening components, 84 and 85, of the front side panels 34 form the interior side panel of the refastenable side seam 66 and the back side panels 35 carrying the first fastening components, 82 and 83, form the exterior side panel of the refastenable side seam 66. While the disclosure herein may focus on the formation of the refastenable side seams 66 in which the back side panels 35 form the exterior side panel and the front side panels 34 form the interior side panel, it should be recognized that the front side panels 34 can form the exterior side panel of the refastenable side seam 66 and the back side panels 35 can form the interior side panel of the refastenable side seam 66. While the disclosure herein may focus on the formation of the refastenable side seam 66 on one side of the absorbent article 20, it should be recognized that a refastenable side seam 66 can be formed on the opposite side of the absorbent article 20 in a similar manner. The refastenable side seams 66 can be formed simultaneously or sequentially on the right and left sides of the absorbent article 20.

Figure 6:
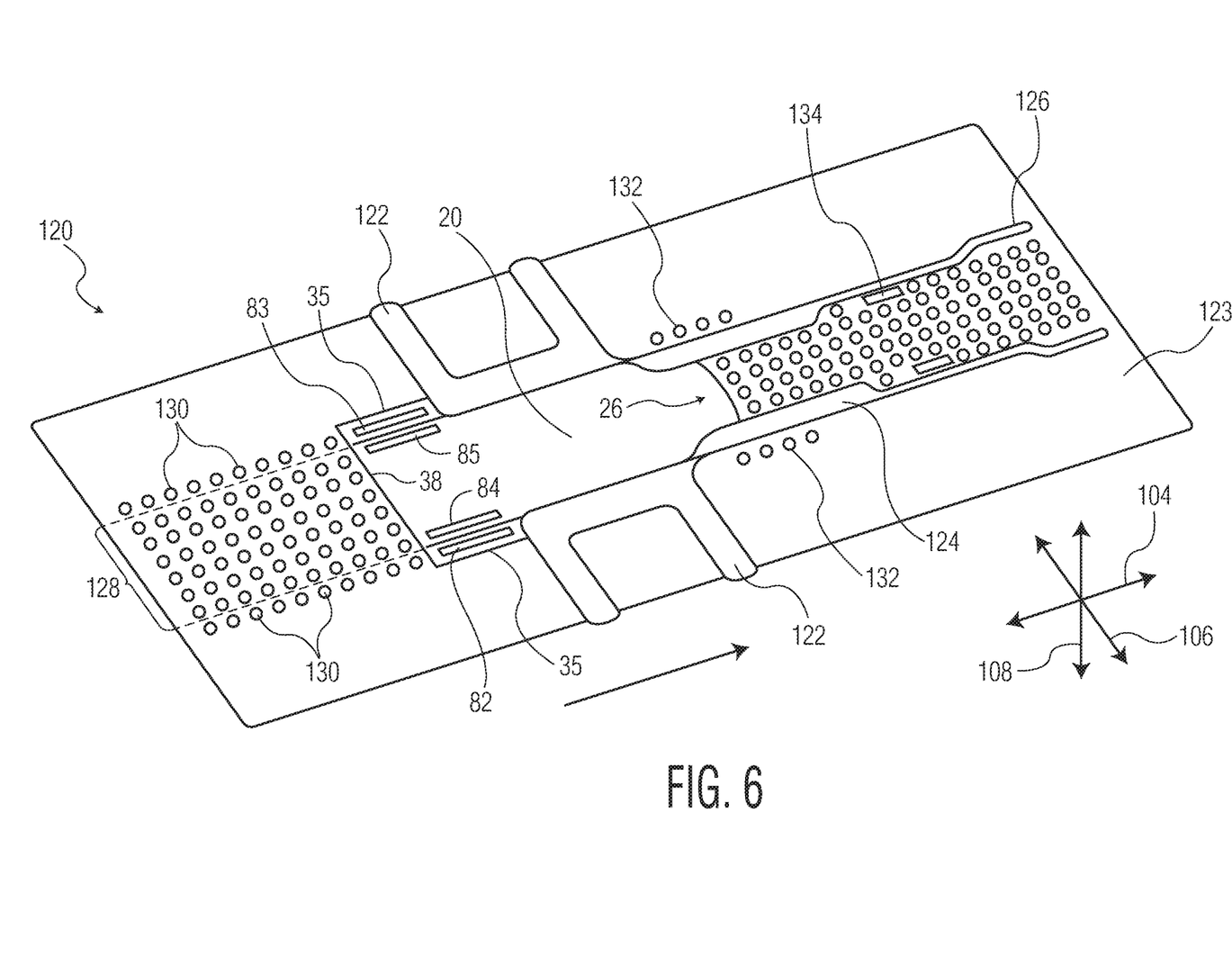
FIG. 6 is an isometric view of an absorbent article being folded in the upper folding conveyor.
Figure 7:
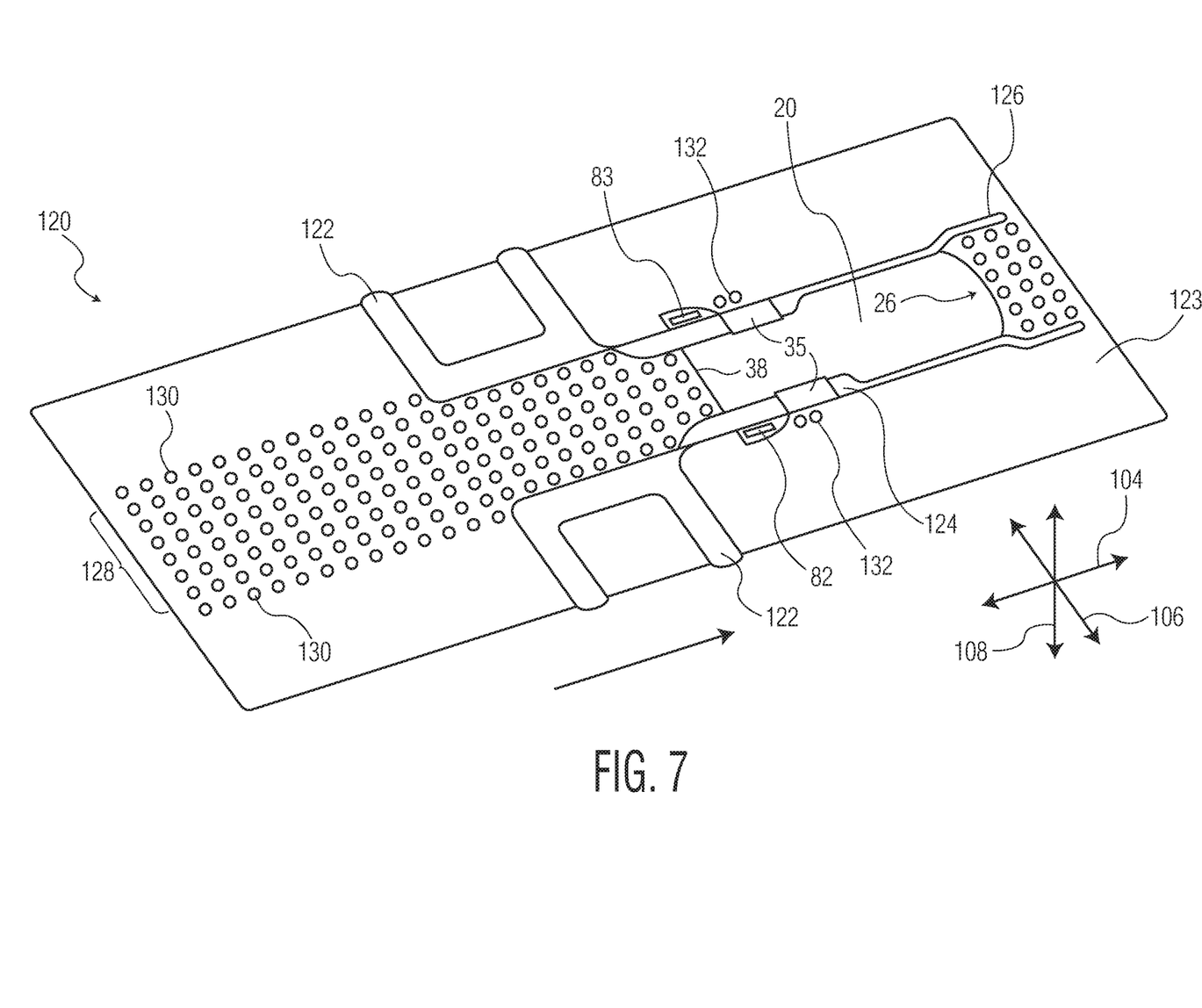
FIG. 7 is an isometric view of an absorbent article being folded in the upper folding conveyor.

In various embodiments, the formation of the refastenable side seams 66 can occur through the use of vacuum pressure and compressed air. FIGS. 6 and 7 provide illustrations of the absorbent article 20 in sequential positions on the upper fastening conveyor 120. The absorbent article 20 can be maintained in position on the upper fastening conveyor 120 through the use of the primary arrangement of holes 128 and a vacuum source. The vacuum source can apply a vacuum through the primary arrangement of holes 128 which can be of sufficient pressure and strength to pull the absorbent article 20 against the belt 123 of the upper fastening conveyor 120. In various embodiments, the upper fastening conveyor 120 can have a vacuum chamber which can operate over a range of vacuum such as, for example, a vacuum of about 2 inches of water or greater below atmospheric pressure. The secondary arrangement of holes 130 can maintain at least the back panels 35 in position on the upper fastening conveyor 120, also through the use of a vacuum source applying a sufficient vacuum through the second arrangement of holes 130. In various embodiments, the vacuum source can apply a vacuum pressure of great enough sufficiency that the front side panels 34 can be maintained in position on the belt 123 of the upper fastening conveyor 120. As the fastening of the side panels, 34 and 35, to each other occurs following the folding of the absorbent article 20, the absorbent article 20 can be in a folded configuration and the crotch region 26 can provide the leading edge of the absorbent article 20 through at least the fastening portion of the manufacturing process.

Referring to FIG. 6, the back side panels 35 can extend in the cross-direction 106 beyond the primary arrangement of holes 128 and the first fastening components, 82 and 83, can face away from the surface of the belt 123 of the upper fastening conveyor 120. The back side panels 35 can be smoothed out or straightened if desired by various means including fluid stabilization devices. In the embodiment illustrated in FIG. 6, the back side panels 35 can be outstretched in the cross-direction 106 and held in that position by the secondary arrangement of holes 130. The front side panels 34 can be positioned adjacent to the back side panels 35. The outer edges 68 of the front side panels 34 are located inward of the outer edges 68 of the back side panels 35 due to the smaller width dimension of the front side panels 34.

The absorbent article 20 will move in the machine direction 104 between the upper fastening conveyor 120 and the lower fastening conveyor. In this movement, the back side panels 35 and the front side panels 34 will pass between the belt 123 and an alignment plate 122. The alignment plate 122 can extend in the machine direction 104 and can bring the front side panels 34 in closer proximity to the back side panels 35. The alignment plate can comprise a low friction material or coating, such as, for example, stainless steel, Teflon, aluminum, ultra-high molecular weight polyethylene (UHMW-PE), polyoxymethylene (acetals), or the like.

Referring to FIG. 7, in various embodiments, each alignment plate 122 can narrow to a fold plate 124 which can form a guide for a consistent fold of the back side panel 35 over the front side panel 34. As the absorbent article 20 continues to move in the machine direction 104 of the manufacturing process, the side panels, 34 and 35, of the absorbent article 20 will pass from between the belt 123 and the alignment plates 122 to between the belt 123 and the fold plates 124. The front side panels 34 and the back side panels 35 will be positioned between the belt 123 and the fold plates 124. Only the back side panels 35 will extend in the cross-direction 106 beyond the fold plates 124. The amount of material of the back side panels 34 extending beyond the fold plates 124 should include the first fastening components, 82 and 83. Compressed air can be forced from a compressed air source and through the compressed air openings 132 to move the material of the back side panels 35 which extend beyond the fold plates 124 up and over the fold plates 124. The back side panels 35, therefore, can have a portion of material which is below the front side panels 34 and between the belt 123 and the fold plate 124 as well as a portion of material which is positioned over the fold plates 124 and in position for the first fastening components, 82 and 82, to be engaged with the second fastening components, 84 and 85, located on the front side panels 34.

As the absorbent article 20 continues through the manufacturing process, the absorbent article will move between the upper fastening conveyor 120 and the lower fastening conveyor. The upper fastening conveyor 120 can have a pair of engagement rollers 134 and the lower fastening conveyor can have a corresponding pair of engagement rollers. As the absorbent article 20 continues to move through the manufacturing process, the absorbent article 20 will move beyond, in the machine direction, the fold plates 124 and the folded material of the back side panels 35 will come into contact with the material of the front side panels 34. This contact between the panels, 34 and 35, will bring into contact the first fastening components, 82 and 83, with the second fastening components, 84 and 85. The side panels, 34 and 35, and the corresponding fastening components, 82, 83, 84 and 85, can pass between the engagement rollers 134 of the upper fastening conveyor 120 and the corresponding engagement rollers of the lower fastening conveyor. The engagement rollers 134 of the upper fastening conveyor 120 and the engagement rollers of the lower fastening conveyor can form a nip through which the side panels, 34 and 35, and the fastening components, 82, 83, 84 and 85, will pass. The nip will cause engagement in the z-direction 108 between the first fastening components, 82 and 83, and the second fastening components, 84 and 84.

The fold plates 124 can extend in the machine direction 104 and can narrow in width into engagement rods 126. Each engagement rod 126 can extend generally in the machine direction 104 for any length dimension as deemed suitable. Each engagement rod 126 can have a portion which can generally be straight in the machine direction 104 and can have a portion which can arch outward in the cross-direction 106. The arch in each engagement rod 126 can widen the distance in the cross direction 126 between the engagement rods 126. Following the engagement in the z-direction 108 of the first fastening components, 82 and 83, with the second fastening components, 84 and 85, the absorbent article 20 will continue to move in the machine direction 104. The back side panel 35 which was folded over the fold plate 124 will remain folded over the engagement rod 126 for the length of the engagement rod 126. As the absorbent article 20 moves in the machine direction, when the absorbent article 20 reaches the arch in the engagement rod 126 the material of the absorbent article 20 will move in the cross-direction 106. Such movement in the cross-direction will further engage the first fastening components, 82 and 83, with the second fastening components, 84 and 85, in the cross-direction 106. Thus, a refastenable side seam 66 of an absorbent article 20 can be engaged in both the z-direction 108 and the cross-direction 106 following the method disclosed herein.

It is to be understood that the manufacturing process described herein regarding bonding of back side panels 35 to front side panels 34 can also be utilized to bond back side panels 35 directly to the outer cover 40 of an absorbent article 20 in the front waist region 22 of the absorbent article 20.

When introducing elements of the present disclosure or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements. Many modifications and variations of the present disclosure can be made without departing from the spirit and scope thereof. Therefore, the exemplary embodiments described above should not be used to limit the scope of the invention.

What is claimed is:

1. A method of forming a side seam of an absorbent article, the method comprising the steps of:
   a. providing an absorbent article comprising:
      i. a machine direction, a cross-direction, and a z-direction;
      ii. a front waist region, a back waist region, and a crotch region extending between and connecting the front waist region and the back waist region;
      iii. a first side panel comprising a first fastening component and located in the front waist region having a first width dimension in the cross-direction; and
      iv. a second side panel comprising a second fastening component and located in the back waist region having a second width dimension in the cross-direction, wherein the second width dimension is larger than the first width dimension;
   b. bringing the first side panel and the second side panel into proximity with each other;
   c. folding the second side panel over the first side panel;
   d. engaging the first fastening component and the second fastening component in the z-direction; and
   e. manipulating the first side panel and the second side panel in the cross-direction to further engage the first fastening component and the second fastening component in the cross-direction.

2. The method of claim 1 wherein the first side panel and the second side panel are brought into proximity by folding the absorbent article.

3. The method of claim 1 wherein the second side panel is a back side panel of the absorbent article.

4. The method of claim 1 wherein the first side panel is a front side panel of the absorbent article.

5. The method of claim 1 wherein the engagement is one of an adhesive engagement or a hook and loop engagement.

6. The method of claim 1 wherein the folding of the second side panel occurs via compressed air.

7. The method of claim 1 wherein the absorbent article is transported in a machine direction of the method and between a pair of fastening conveyors.

8. The method of claim 7 wherein one of the fastening conveyors has a fold plate around which the second side panel folds.

9. The method of claim 8 wherein the first side panel and the second side panel pass between a belt of the fastening conveyor and the fold plate of the fastening conveyor.

10. The method of claim 8 wherein the second side panel extends in the cross-direction beyond the fold plate.

11. The method of claim 8 wherein the pair of fastening conveyors further have a pair of engagement rollers.

12. The method of claim 8 wherein the fastening conveyor further has an engagement rod.

13. The method of claim 12 wherein the engagement rod has an arch in the cross-direction.

* * * * *